United States Patent [19]

Aya et al.

[11] 3,996,041
[45] Dec. 7, 1976

[54] NOVEL AMIDOTHIONOPHOSPHORIC ACID ESTERS AND THEIR USE AS HERBICIDES

[75] Inventors: Masahiro Aya; Shigeo Kishino; Nobuo Fukazawa; Toyohiko Kume, all of Tokyo, Japan

[73] Assignee: Bayer Aktiengesellschaft, Leverkusen, Germany

[22] Filed: Apr. 16, 1975

[21] Appl. No.: 568,635

Related U.S. Application Data

[63] Continuation of Ser. No. 319,079, Dec. 27, 1972, abandoned.

[30] Foreign Application Priority Data

Dec. 27, 1971 Japan .......................... 47-105444

[52] U.S. Cl. .................................................. 71/87
[51] Int. Cl.² ........................................ A01N 9/36
[58] Field of Search ........................................ 71/87

[56] References Cited

UNITED STATES PATENTS

| | | | |
|---|---|---|---|
| 3,010,986 | 11/1961 | Reetz | 71/87 |
| 3,511,633 | 5/1970 | Kleiman et al. | 71/87 |
| 3,636,143 | 1/1972 | Schrader et al. | 71/87 |
| 3,644,600 | 2/1972 | Beriger | 71/87 |
| 3,784,635 | 1/1974 | Theissen | 71/105 |
| 3,819,754 | 6/1974 | Aya et al. | 71/87 |

OTHER PUBLICATIONS

Mel'nikov et al., "Herbicide Activity of Ester Amides, etc;" (1969) CA72, No. 20766u, (1970).

*Primary Examiner*—Glennon H. Hollrah
*Attorney, Agent, or Firm*—Burgess, Dinklage & Sprung

[57] ABSTRACT

Amidothionophosphonic acid ester compounds of the formula:

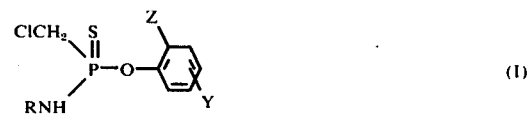

(I)

in which
R is alkyl of from 1 to 6 carbon atoms or lower cycloalkyl;
Y is hydrogen, halogen or alkyl or alkoxy of from 1 to 6 carbon atoms; and
Z is nitro or cyano;

are outstandingly effective as herbicides and exhibit particularly selective action.

18 Claims, No Drawings

NOVEL AMIDOTH IONOPHOSPHORIC ACID ESTERS AND THEIR USE AS HERBICIDES

This is a continuation of application Ser. No. 319,079, filed Dec. 27, 1972, now abandoned.

The present invention relates to certain new amidothionophosphonic acid ester compounds, to herbicidal compositions containing such compounds, and to their use as herbicides.

From the specification of U.S.S.R. Pat. No. 216,380 it is known that the amidothionophosphonic acid ester of the formula

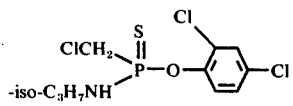

has a herbicidal activity.

The present invention provides amidothionophosphonic acid esters of the general formula

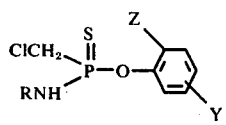

in which
R is alkyl of from 1 to 6 carbon atoms or lower cycloalkyl;
Y is hydrogen, halogen or alkyl or alkoxy of from 1 to 6 carbon atoms; and
Z is nitro or cyano.

The compounds of the formula (I) exhibit an excellent herbicidal activity.

R in formula (I) is preferably alkyl of from 1 to 4 carbon atoms (namely methyl, ethyl, n-propyl, isopropyl, n-butyl, isobutyl, sec.-butyl or tert.-butyl), cyclopentyl or cyclohexyl, while Y is preferably hydrogen, halogen (that is, fluorine, chlorine, bromine or iodine), alkyl of from 1 to 4 carbon atoms or alkoxy of from 1 to 4 carbon atoms (namely methoxy, ethoxy, n-propoxy, isopropoxy, n-butoxy, isobutoxy, sec.-butoxy or tert.-butoxy). These compounds are preferred because of their exceptional herbicidal activity and/or selectivity.

The compounds of this invention, as stated above, have excellent herbicidal activity. Their activity is superior to the herbicidal activity shown by the compound described in U.S.S.R. Pat. No. 216,380, to which reference has been made above, or by other compounds having structural formulas similar to formula (I). In particular, when the active compounds of this invention are applied to paddy-field weeds, they exhibit an excellent herbicidal activity against the grasses, broad-leafed weeds and perennial weeds without showing any phytotoxicity to rice plants.

The present invention also provides a process for the production of an amidothionophosphonic acid ester of the formula (I) in which
a. a phenol of the general formula

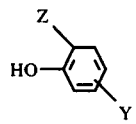

is reacted, as such (optionally in the presence of an acid-binding agent) or as a metal or ammonium salt thereof, with a chloromethane thionophosphonamide chloride of the general formula

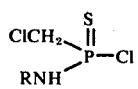

or (b) a chloromethane thionophosphonyl chloride of the general formula

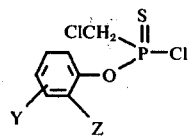

is reacted (optionally in the presence of an acid-binding agent) with an amine of the general formula

in which formulas
R, Y and Z have the meanings stated above.
Process variant (a) may be illustrated by the following formula scheme:

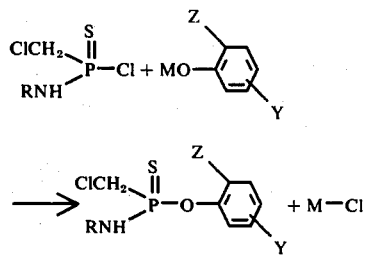

in which
M is hydrogen or an alkali metal (preferably sodium or potassium) atom.

Examples of the chloromethane thionophosphonamide chlorides of the general formula (II) are N-methyl-chloromethane thionophosphonamide chloride, N-ethyl-chloromethane thionophosphonamide chloride, N-n-(or iso-)propyl-chloromethane thionophosphonamide chloride, N-n-(or iso- or sec.-)butyl-chloromethane thionophosphonamide chloride and N-cyclohexylchloromethane thionophosphonamide chloride.

Examples of the phenols of general formula (III) are 2-nitrophenol, 2-cyanophenol, 2nitro-4-methylphenol, 2-cyano-4-methylphenol, 2-nitro-4-ethylphenol, 2-nitro-4-tert.-butylphenol, 2-nitro-4-chlorophenol, 2-cyano-4-chlorophenol, 2-nitro-4-bromophenol, and 2-nitro-4-methoxyphenol.

Process variant (b) may be illustrated by the following reaction scheme:

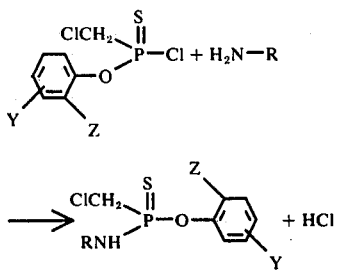

Examples of the chloromethane thionophosphonyl chlorides of the general formula (IV) are 0-2-nitrophenyl-chloromethane thionophosphonyl chloride, 0-2-cyanophenyl-chloromethane thionophosphonyl chloride, 0-(2-nitro-4-methylphenyl)-chloromethane thionophosphonyl chloride, 0-(2-cyano-4-methylphenyl)-chloromethane thionophosphonyl chloride, 0-(2-nitro-4-ethylphenyl)-chloromethane thionophosphonyl chloride, 0-(2-nitro-4-tert.-butylphenyl)-chloromethane thionophosphonyl chloride, 0-(2-nitro-4-tert.-butylphenyl)-chloromethane thionophosphonyl chloride, 0-(2-nitro-4-chlorophenyl)-chloromethane thionophosphonyl chloride, 0-(2-cyano-4-chlorophenyl)-chloromethane thionophosphonyl chloride, 0-(2-nitro-4-bromophenyl)-chloromethane thionophosphonyl chloride, and 0-(2-nitro-4-methoxyphenyl)-chloromethane thionophosphonyl chloride.

Examples of the amines of the general formula (V) are methylamine, ethylamine, n-propylamine, isopropylamine, n-butylamine, isobutylamine, sec.-butylamine, cyclopentylamine and cyclohexylamine.

The synthesis of the active compounds according to either of the above process variants is preferably conducted in a solvent or diluent. For this purpose, practically any inert organic solvent or diluent may be used, especially aliphatic, alicyclic and aromatic hydrocarbons (which may be chlorinated), such as hexane, cyclohexane, petroleum ether, ligroin, benzene, toluene, xylenes, methylene chloride, chloroform, carbon tetrachloride, mono-, di- and tri- chloroethylenes, and chlorobenzene; ethers, such as diethyl ether, methyl ethyl ether, di-isopropyl ether, dibutyl ether, ethylene oxide, dioxane and tetrahydrofuran; ketones, such as acetone, methyl ethyl ketone, methyl isobutyl ketone and methyl isopropyl ketone; nitriles, such as acetonitrile, propionitrile and acrylonitrile; alcohols, such as methanol, ethanol, isopropanol, butanol and ethylene glycol; esters, such as ethyl acetate and amyl acetate; acid amides, such as dimethyl formamide and dimethyl acetamide; sulphoxides and sulphones, such as dimethyl sulphoxide and sulphoran; and bases, such as pyridine. Water may also be used for this purpose.

Either of the above process variants may involve the use of an acid-binding agent. For this purpose, there may be used any customary acid-binder, such as a hydroxide, carbonate, bicarbonate or alcoholate of an alkali metal, or a tertiary amine, for example triethylamine, diethylaniline or pyridine. However, the reaction of process variant (a) may be effected in the absence of such an acid-binder by reacting a metal or ammonium salt of the appropriate phenol (III) with the chloromethane thionophosphonyl chloride; this method of working can give a high yield of the intended product having a high degree of purity.

In either of the above process variants, the reaction may be effected at temperatures within a wide range; generally, the reaction is carried out at from −20° C to the boiling point of the reaction mixture, preferably at from 0° to 100° C or to the boiling point of the reaction mixture, whichever is the lower.

The preparation of the compounds of this invention is illustrated by the following preparative Examples.

EXAMPLE 1

Preparation of 0-(2-nitro-4-methylphenyl)-N-isopropyl chloromethane thionophosphonamide ester 15.3 g (0.1 mole) of 2-nitro-4-methylphenol were dissolved in 100 ml of methyl ethyl ketone, and 14 g (0.11 mole) of potassium carbonate were added to the solution, which was then agitated at 50° C for 30 minutes. At 30°–35° C, 20.6 g (0.1 mole) of N-isopropyl chloromethane thionophosphonamide chloride were added dropwise to the solution. The reaction mixture was agitated at 50°–55° C for 4 hours to complete the reaction. The methyl ethyl ketone was removed by distillation and 100 ml of benzene were added to the residue. The mixture was washed with water, with 2% aqueous potassium hydroxide solution and again with water and dried over anhydrous sodium sulfate. Removal of the benzene by distillation gave 25 g (yield = 70%) of 0-(2-nitro-4-methylphenyl)-N-isopropyl chloromethane thionophosphonamide ester characterized by a refractive index $n_D^{20}$ of 1.5737. The product is hereinafter referred to as compound No. 1; it has the following formula:

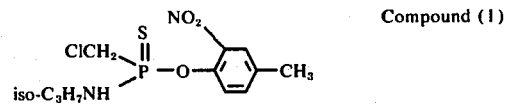

Compound (1)

EXAMPLE 2

Preparation of 0-(2-nitro-4-methylphenyl)-N-cyclohexyl chloromethane thionophosphonamide ester 30 g (0.1 mole) of 0-(2-nitro-4-methylphenyl)-chloromethane thionophosphonyl chloride were dissolved in 100 ml of benzene, and 19.8 g of cyclohexylamine were added dropwise to the solution at 5°–10° C. The mixture was agitated at room temperature for 2 hours and then at 35°–40° C for 2 hours, following which it was air-cooled, washed with water, dilute (1%) hydrochloric acid, 2% aqueous potassium hydroxide solution and again with water, and dried over anhydrous sodium sulfate. Distillation of the benzene gave 29 g (yield = 82%) of 0-(2-nitro-4-methylphenyl)-N-cyclohexyl chloromethane thionophosphonamide ester characterized by a refractive index $n_D^{20}$ of 1.5818. The product is hereinafter referred to as Compound No. 2 and has the following formula:

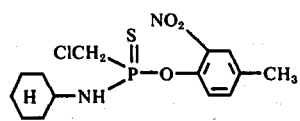

Compound (2)

The compounds characterized in the following Table were prepared by methods analogous to those described above.

Table 1

$$\underset{RNH}{\overset{ClCH_2}{>}}\overset{S}{\underset{\|}{P}}-C\overset{Z}{\underset{Y}{\diagdown}}\diagup \qquad (I)$$

| Compound No. | R | Z | Y | Refractive Index $n_D^{20}$ | Process Variant |
|---|---|---|---|---|---|
| 3 | n-C$_3$H$_7$ | NO$_2$ | 4-CH$_3$ | 1.5796 | (b) |
| 4 | iso-C$_3$H$_7$ | NO$_2$ | H | 1.5790 | (a) |
| 5 | iso-C$_3$H$_7$ | NO$_2$ | 4-CH$_3$O | 1.5780 | (a) |
| 6 | iso-C$_3$H$_7$ | NO$_2$ | 4-tert-C$_4$H$_9$ | 1.5555 | (a) |
| 7 | iso-C$_3$H$_7$ | NO$_2$ | 4-Cl | 1.5835 | (a) |
| 8 | sec-C$_4$H$_9$ | NO$_2$ | 4-CH$_3$ | 1.5690 | (b) |
| 9 | iso-C$_3$H$_7$ | CN | H | 1.5690 | (b) |
| 10 | iso-C$_3$H$_7$ | CN | 4-Cl | 1.5750 | (a) |

As disclosed hereinabove, the instant compounds exhibit marked herbicidal activity.

When the compounds of this invention are applied in small amounts to upland weeds, especially in the pre-emergence treatment thereof, they exhibit an excellent selective herbicidal activity without showing ay phytotoxicity to the cultivated plants. In this regard, the compounds of the present invention are superior to many conventional herbicides.

When the compounds of this invention are used in large amounts (e.g., 5.0–40 kg per hectare calculated as active ingredient), they exhibit a non-selective herbicidal activity. However, when they are used in small amounts (i.e., 1.0–5.0 kg per hectare), they exhibit an excellent selective herbicidal activity. For this reason, they can be used as germination-preventing agents, especially as weed-controlling agents. The term "weed" is used in its broadest sense in this specification to include all plants growing in places where their growth is not desired.

The active compounds according to the invention exhibit a herbicidal activity against, for example, the folowing plants: dicotyledons, such as cleavers (Galium), chickweed (Stellaria), chamomile (Matricaria), gallant soldier (Galinsoga), goosefoot (Chenopodium), annula nettle (Urtica), grounsel (Senecio), amaranth (Amaranthus) and common purslane Portulaca); and monocotyledons, such as timoth (Phleum), bluegrass (Poa), fescue (Festuca), goosegrass (Eleusine), foxtail (Setaria), ryegrass (Lolium) fingergrass (Digitaria) and barnyard grass (Echinochloa). However, in small applied amounts, they show no phytotoxicity towards such dicotyledons as mustard (Sinapis), cress (Lepidium), cotton (Gossypium), beets (Beta), carrots (Daucus), beans (Phaseolus), cabbage (Brassica), potatoes (Solanum) and coffee (Coffea) and such monocotyledons as maize (Zea), rice (Oryza), oats (Avena), barley (Mordeum), wheat (Triticum), millet (Panicum) and sugar cane (Saccharum).

The compounds of this invention, owing to their excellent biological activities, can be used to increase production and to save labor in agriculture. They may therefore be used with advantage in agricultural applications.

The active compounds according to the present invention can be converted into the usual formulations, such as solutions, emulsions, suspensions, tablets, fumigants, aerosols, powders, pastes and granulates. These may be produced in known manner, for example, by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, ethylene chloride or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

Possible adjuvants include organic matter, stabilizers, adhesive agents, for example soap, calcium, calcium caseinate, sodium alginate, polyvinyl alcohol, steeping agents, coumarone (or indene) resins or polyvinyl butyl ether, combustible materials (for fumigants), for example nitrites, zinc dust or dicyandiamide, oxygen-yielding substances, for example perchlorates or dichromates, phytotoxicity-reducing substances, for example zinc sulfate, ferrous chloride or copper nitrate, substances for prolonging the biological effect, for example chlorinated terphenyls, emulsion-stabilizing substances, for example casein, gum tragacanth and carboxymethyl cellulose (polyvinyl alcohol also being suitable for this purpose), and synergistic agents.

The formulations contain, in general, from 0.1 to 95%, preferably from 0.5 to 90%, by weight of the active compound.

The compounds of the present invention can, if desired, be applied with other agricultural chemicals such as insecticides, acaricides, nematocides, antiviral agents, herbicides and plant-growth regulators, as well as with fertilizers.

The ready-to-use preparations (which may be prepared from suitable formulations by, for instance, dilution with water) may be applied—in either pre-emergence or post-emergence treatments—in any usual manner, for instance, by spraying, such as liquid spraying, misting, atomizing, dusting, scattering, watering, pouring, fumigating, by soil application, such as mixing, sprinkling, vaporizing and irrigation, by surface application, such as painting, banding and dressing (dust-coating), or by immersion.

The amount of the active compound in the ready-to-use preparation is generally from 0.0001–20% by weight, preferably 0.005–10% by weight. The quantity of the active ingredient can be varied according to the type of preparation used, the method, purpose, time and place of the application and the growth state of the weeds to be controlled.

The compounds to be used according to the present invention may be also used in accordance with the well-known ultralow-volume (ULV) process. According to this method, it is possible to use a concentration of the active ingredient of up to 95% by weight, or even to apply the active compound alone.

The dosage per unit area is generally 3 to 1000 g, preferably 30 to 600 g, by weight of active compound per 10 acres. However, it is possible to increase or reduce the usual amount and, in special cases, it may actually be necessary to do so.

The present invention also provides a herbicidal composition containing as active ingredient a compound of the present invention in admixture with a solid or liquefied gaseous diluent or carrier or in admixture with a liquid diluent or carrier or in admixture with a liquid diluent or carrier containing a surface active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides methods of providing crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal compositions of this invention are illustrated by the following Examples, in which the compounds of this invention are identified by the numbers assigned to them in Examples 1 and 2 and Table 1. Parts are by weight.

Example (i) (Wettable Powder)

15 Parts of Compound No. 2, 80 parts of a 1:5 mixture of diatomaceous earth and kaolin and 5 parts of an emulsifier (a polyoxyethylene alkyl aryl ether) were ground and mixed together to form a wettable powder. It was diluted with water before being applied.

Example (ii) (Emulsifiable Liquor)

30 Parts of Compound No. 1, 30 parts of xylene, 30 parts of methylnaphthalene and 10 parts of an emulsifier (a polyoxyethylene alkyl aryl ether) were mixed by stirring to form an emulsifiable liquor. It was diluted with water and applied by spraying.

Example (iii) (Dust)

2 Parts of Compound No. 7 and 98 parts of a 1:3 mixture of talc and clay were ground and mixed together to form a dust. This was applied by scattering.

Example (iv) (Dust)

1.5 Parts of Compound No. 5, 0.5 part of isopropyl hydrogen phosphate (PAP) and 98 parts of a 1:3 mixture of talc and clay were ground and mixed together to form a dust. This was applied by scattering.

Example (v) (Granules)

25 Parts of water were added to a mixture of 10 parts of Compound No. 2, 10 parts of bentonite, 78 parts of a 1:3 mixture of talc and clay and 2 parts of lignin sulfonate. The resulting mixture was intimately blended and finely divided by means of an extruding granulator to obtain granules of 20–40 mesh, which were dried at 40°–50° C. The resulting granules were applied by spraying.

Example (vi) (Granules)

95 Parts of clay particles of a size distribution of 0.2–2 mm were put into a rotary mixer and a solution of 5 parts of Compound No. 10 in an organic solvent was sprayed onto the particles being rotated, thereby wetting the particles homogeneously. They were then dried at 40°–50° C to form coated granules, which were applied by spraying.

Example (vii) (Oil Preparation)

0.5 Part of Compound No. 4, 20 parts of methylnaphthalene, and 79.5 parts of kerosene were mixed by stirring to form an oil preparation. It was applied by spraying.

Compared with active compounds of similar structures which have been described in the literature or known compounds exhibiting a similar direction of activity, the compounds of this invention are characterized by substantially improved effects and by a very low toxicity to warm-blooded animals. Accordingly, the compounds of this invention are of great utility.

The herbicidal activity of the compounds of this invention is illustrated in the following Examples in which the active compounds of this invention are identified by the number assigned to them in Examples 1 and 2 and Table 1.

Example A

Test on effects against paddy-field weeds in a water-applied pre-emergence treatment:

Preparation of Sample Formulation

Solvent: 5 parts by weight of acetone
Emulsifier: 1 Part by weight of benzyloxypolyglycol ether In order to prepare a suitable formulation of an active compound, one part by weight of the active compound was mixed with the above amount of the solvent containing the above amount of the emulsifier, and the mixture was diluted with water to form an aqueous formulation containing the active compound at a prescribed concentration.

Test Procedure

Wagner pots (1/5000 are) were charged with soil from a rice paddy field. Two seedlings of rice (Kinmaze variety) at the three- or four-leafed stage (about 15 cm in height) prior to tillering were planted in each pot. Seeds of barnyard grass, flat sedges and broad-leafed weeds were sown, and the soil was infected with spikerush and watered to a depth of 6 cm. The active compound in the form of an emulsion prepared in the above manner was applied to the water in a prescribed amount.

After the chemical treatment, water was leaked from each pot for two days in an amount corresponding to 2–3 cm depth per day; thereafter, the depth of water was maintained at about 3 cm. Four weeks after the chemical treatment, the herbicidal (weed-controlling) effect and the degree of phytotoxicity to the rice plants were evaluated on respective scales of from 0 to 5 as shown below.

| Herbicidal Effect | Weed Killing Ratio |
| --- | --- |
| 5 | more than 95% (withering) |
| 4 | more than 80% up to 95% |
| 3 | more than 50% up to 80% |
| 2 | more than 30% up to 50% |
| 1 | more than 10% up to 30% |
| 0 | 10% or less (no effect) |

| Degree of Phytotoxicity | Phytotoxicity Ratio |
| --- | --- |
| 5 | more than 90% (fatal damage) |
| 4 | more than 50% up to 90% |
| 3 | more than 30% up to 50% |
| 2 | more than 10% up to 30% |
| 1 | 10% or less |
| 0 | No damage |

The results are shown in Table A.

Table A

| Compound No. | Active Compound concentration (g/10 are) | Herbicidal Effect Barnyard grass | Flat sedge | Spike-rush | Broad-leaved weeds | Phytotoxicity Rice plant |
| --- | --- | --- | --- | --- | --- | --- |
| 1 | 300 | 5 | 5 | 5 | 5 | 0 |
|  | 150 | 5 | 5 | 5 | 5 | 0 |
|  | 75 | 5 | 5 | 4 | 5 | 0 |
| 2 | 300 | 5 | 5 | 5 | 5 | 0 |
|  | 150 | 5 | 4 | 4 | 4–5 | 0 |
|  | 75 | 4 | 4 | 3 | 4 | 0 |
| 3 | 300 | 5 | 5 | 5 | 5 | 0 |
|  | 150 | 5 | 5 | 4 | 4 | 0 |
|  | 75 | 4 | 4 | 4 | 4 | 0 |
| 4 | 300 | 5 | 5 | 5 | 5 | 0 |
|  | 150 | 4–5 | 4 | 4 | 4 | 0 |
|  | 75 | 4 | 3 | 3 | 4 | 0 |
| 5 | 300 | 5 | 5 | 5 | 5 | 0 |
|  | 150 | 5 | 4 | 4 | 4 | 0 |
|  | 75 | 5 | 4 | 3 | 4 | 0 |
| 6 | 300 | 5 | 5 | 5 | 5 | 0 |
|  | 150 | 5 | 5 | 5 | 5 | 0 |
|  | 75 | 4 | 4 | 4 | 4 | 0 |
| 7 | 300 | 5 | 5 | 5 | 5 | 0 |
|  | 150 | 5 | 5 | 4 | 5 | 0 |
|  | 75 | 5 | 4 | 4 | 4–5 | 0 |
| 8 | 300 | 5 | 5 | 5 | 5 | 0 |
|  | 150 | 5 | 5 | 5 | 5 | 0 |
|  | 75 | 5 | 5 | 4 | 5 | 0 |
| 9 | 300 | 5 | 5 | 5 | 5 | 0 |
|  | 150 | 4 | 4 | 4 | 4 | 0 |
|  | 75 | 4 | 3 | 3 | 3 | 0 |
| 10 | 300 | 5 | 5 | 5 | 5 | 0 |
|  | 150 | 5 | 5 | 4 | 5 | 0 |
|  | 75 | 4 | 4 | 4 | 4–5 | 0 |
| VI (comparison) | 300 | 0 | 0 | 0 | 0 | 0 |
|  | 150 | 0 | 0 | 0 | 0 | 0 |
|  | 75 | 0 | 0 | 0 | 0 | 0 |
| VII (comparison) | 300 | 0 | 0 | 0 | 0 | 0 |
|  | 150 | 0 | 0 | 0 | 0 | 0 |
|  | 75 | 0 | 0 | 0 | 0 | 0 |
| VIII (comparison) | 300 | 0 | 0 | 0 | 0 | 0 |
|  | 150 | 0 | 0 | 0 | 0 | 0 |
|  | 75 | 0 | 0 | 0 | 0 | 0 |
| IX (comparison) | 300 | 4 | 3 | 1 | 3 | 0 |
|  | 150 | 2 | 1 | 0 | 2 | 0 |
|  | 75 | 0 | 0 | 0 | 0 | 0 |
| X (comparison) | 300 | 4 | 3 | 2 | 3 | 0 |
|  | 150 | 2 | 1 | 0 | 2 | 0 |
|  | 75 | 0 | 0 | 0 | 0 | 0 |
| XI (comparison) | 1000 | 5 | 5 | 4 | 4 | 0 |
|  | 500 | 2 | 2 | 0 | 0 | 0 |
|  | 250 | 0 | 0 | 0 | 0 | 0 |
| XII (comparison) | 500 | 5 | 5 | 5 | 5 | 4 |
|  | 250 | 5 | 5 | 4 | 5 | 3 |
|  | 125 | 2 | 4 | 0 | 3 | 1 |

Notes:
(i) Comparison (VI) 0-(3-nitrophenyl)-N-isopropyl chloromethane thionophosphonamide
Comparison (VII) 0-(4-nitrophenyl)-N-isopropyl chloromethane thionophosphonamide
Comparison (VIII) 0-(4-cyanophenyl)-N-isopropyl chloromethane thionophosphonamide
Comparison (IX) 0-(2,4-dichlorophenyl-N-iso-propyl chloromethane thionophosphonamide (compound disclosed in U.S.S.R. Patent No. 216,380)
Comparison (X) 0-(2,4-dichlorophenyl)-N-iso-propyl-O-ethyl thionophosphoroamide (tradename: Zytron)
Comparison (XI) pentachlorophenol (commercially available product)

Table A-continued

| Compound No. | Active Compound concentration (g/10 are) | Herbicidal Effect | | | Broad-leaved weeds | Phytotoxicity Rice plant |
|---|---|---|---|---|---|---|
| | | Barnyard grass | Flat sedge | Spike-rush | | |
| Comparison (XII) | | 2,4-dichlorophenyl-4'-nitrophenyl ether (commercially available product) | | | | |

(ii) Broad-leafed weeds include monochoria, *Rotala indica*, false pimpernel and *Dopatrium junceum*.

Example B

Test on effects against paddy-field weeds in water-applied post-emergence treatment:

Wagner pots (1/5000 are) were charged with soil from a rice paddy field. Two seedlings of rice (Kinmaze variety) at the three- or four-leafed stage (about 15 cm in height) prior to tillering were planted in each pot. Seeds of barnyard grass, flat sedge and broad-leafed weeds were sown, and the soil was infected with spike-rush. Thereafter, the soil was kept in a wet state. When the barnyard grass had grown to about the two-leafed stage (about 7-9 days after sowing), water was added to the pot to a depth of about 6 cm. The active compound in the form of an emulsion prepared in the manner described in Example A was applied in a prescribed amount.

After the chemical treatment, water was leaked from each pot for 2 days in an amount corresponding to 2-3 cm depth per day, and thereafter the depth of water was maintained at about 3 cm. Four weeks after the chemical treatment, the herbicidal (weed-controlling) effect and degree of phytotoxicity towards the rice plants were evaluated on the scales described in Example A.

The results are shown in Table B.

Table B

| Compound No. | Active compound concentration (g/10 are) | Herbicidal Effect | | | Broad-leaved weeds | Phytotoxicity Rice plant |
|---|---|---|---|---|---|---|
| | | Barnyard grass | Sedge | Spike-rush | | |
| 1 | 400 | 5 | 5 | 5 | 5 | 0 |
| | 200 | 5 | 5 | 4 | 5 | 0 |
| | 100 | 4-5 | 5 | 4 | 5 | 0 |
| 2 | 400 | 4-5 | 5 | 5 | 5 | 0 |
| | 200 | 4 | 4 | 4 | 4 | 0 |
| | 100 | 3 | 4 | 3 | 4 | 0 |
| 3 | 400 | 5 | 5 | 5 | 5 | 0 |
| | 200 | 4 | 5 | 4 | 4 | 0 |
| | 100 | 3 | 4 | 3 | 3 | 0 |
| 4 | 400 | 5 | 5 | 5 | 5 | 0 |
| | 200 | 4 | 4-5 | 4 | 4 | 0 |
| | 100 | 3 | 4 | 3 | 3 | 0 |
| 5 | 400 | 5 | 5 | 5 | 5 | 0 |
| | 200 | 4 | 5 | 4 | 4 | 0 |
| | 100 | 4 | 4 | 3 | 4 | 0 |
| 6 | 400 | 5 | 5 | 5 | 5 | 0 |
| | 200 | 4 | 4 | 4 | 4 | 0 |
| | 100 | 3 | 3 | 3 | 4 | 0 |
| 7 | 400 | 5 | 5 | 5 | 5 | 0 |
| | 200 | 5 | 5 | 4 | 5 | 0 |
| | 100 | 4 | 4 | 3 | 5 | 0 |
| 8 | 400 | 5 | 5 | 5 | 5 | 0 |
| | 200 | 5 | 5 | 4 | 5 | 0 |
| | 100 | 4-5 | 5 | 3 | 5 | 0 |
| 9 | 400 | 5 | 5 | 5 | 5 | 0 |
| | 200 | 4 | 4-5 | 4 | 4 | 0 |
| | 100 | 3 | 4 | 3 | 3 | 0 |
| 10 | 400 | 5 | 5 | 5 | 5 | 0 |
| | 200 | 5 | 5 | 4 | 5 | 0 |
| | 100 | 4 | 4 | 3 | 5 | 0 |
| VI (comparison) | 400 | 0 | 0 | 0 | 0 | 0 |
| | 200 | 0 | 0 | 0 | 0 | 0 |
| | 100 | 0 | 0 | 0 | 0 | 0 |
| VII (comparison) | 400 | 0 | 0 | 0 | 0 | 0 |
| | 200 | 0 | 0 | 0 | 0 | 0 |
| | 100 | 0 | 0 | 0 | 0 | 0 |
| VIII (comparison) | 400 | 0 | 0 | 0 | 0 | 0 |
| | 200 | 0 | 0 | 0 | 0 | 0 |
| | 100 | 0 | 0 | 0 | 0 | 0 |
| IX (comparison) | 400 | 3 | 0 | 0 | 3 | 0 |
| | 200 | 2 | 0 | 0 | 2 | 0 |
| | 100 | 0 | 0 | 0 | 0 | 0 |
| X (comparison) | 400 | 3 | 0 | 0 | 3 | 0 |
| | 200 | 2 | 0 | 0 | 3 | 0 |
| | 100 | 0 | 0 | 0 | 0 | 0 |
| XI (comparison) | 1000 | 3 | 3 | 0 | 2 | 0 |
| | 500 | 0 | 0 | 0 | 0 | 0 |
| | 250 | 0 | 0 | 0 | 0 | 0 |
| XII (comparison) | 500 | 4 | 5 | 5 | 4 | 4 |
| | 250 | 2 | 3 | 0 | 2 | 3 |

Table B-continued

| Compound No. | Active compound concentration (g/10 are) | Herbicidal Effect Barnyard grass | Sedge | Spike-rush | Broad-leaved weeds | Phytotoxicity Rice plant |
| --- | --- | --- | --- | --- | --- | --- |
|  | 125 | 0 | 0 | 0 | 0 | 1 |

Note:
The comparison compounds and broad-leafed weeds are as identified in the footnotes to Table A.

Example C

Test on effects on various upland plants in a pre-emergence treatment.

Seeds of upland rice, other cultivated plants and weeds were sown in soil-charged pots (30 cm × 30 cm) and, 24 hours later, the active compound in the form of an emulsion prepared as described in Example A was applied to the soil surface in an amount (calculated as the active compound) of 500 g, 250 g or 125 g per 10 ares. Three weeks after the chemical treatment, the damage done to the upland rice and other cultivated plants and to the weeds was evaluated on a scale from 0 to 5 as shown below:

Degree of Damage

0: no influence
1: slight damage and slight growth retardation
2: considerable damage and considerable growth retardation
3: extreme damage and only 50% of seeds germinated
4: only 25% of seeds germinated
5: complete extinction with no germination The results are shown in Table C.

Table C

| Compound No. | Active compound concentration (g/10 are) | Barnyard grass | Finger grass | Flat sedge | Polygonum blumei | Goosefoot | Cock's foot | Common purslane | Rice | Radish | Carrot | Maize | Soy bean |
| --- | --- | --- | --- | --- | --- | --- | --- | --- | --- | --- | --- | --- | --- |
| 1 | 500 | 5 | 5 | 5 | 5 | 5 | 5 | 5 | 2 | 2 | 1 | 0 | 1 |
|  | 250 | 5 | 5 | 5 | 5 | 5 | 5 | 5 | 0 | 0 | 0 | 0 | 0 |
|  | 125 | 5 | 5 | 5 | 4 | 5 | 4 | 5 | 0 | 0 | 0 | 0 | 0 |
| 2 | 500 | 5 | 5 | 5 | 5 | 5 | 5 | 5 | 1 | 1 | 0 | 0 | 0 |
|  | 250 | 4 | 4 | 4 | 4 | 4 | 4 | 4 | 0 | 0 | 0 | 0 | 0 |
|  | 125 | 3 | 3 | 3 | 3 | 3 | 2 | 3 | 0 | 0 | 0 | 0 | 0 |
| 3 | 500 | 5 | 5 | 5 | 5 | 5 | 5 | 5 | 2 | 2 | 0 | 0 | 0 |
|  | 250 | 4-5 | 4-5 | 4 | 4 | 5 | 4 | 5 | 0 | 1 | 0 | 0 | 0 |
|  | 125 | 4 | 4 | 4 | 3 | 4 | 3 | 4 | 0 | 0 | 0 | 0 | 0 |
| 4 | 500 | 5 | 5 | 5 | 5 | 5 | 5 | 5 | 1 | 1 | 0 | 0 | 0 |
|  | 250 | 4 | 4 | 4 | 4 | 4 | 4 | 4 | 0 | 0 | 0 | 0 | 0 |
|  | 125 | 3 | 3 | 3 | 3 | 4 | 2 | 3 | 0 | 0 | 0 | 0 | 0 |
| 5 | 500 | 5 | 5 | 5 | 5 | 5 | 5 | 5 | 2 | 2 | 1 | 0 | 0 |
|  | 250 | 5 | 5 | 5 | 5 | 5 | 4 | 5 | 0 | 0 | 0 | 0 | 0 |
|  | 125 | 4-5 | 4 | 5 | 4 | 5 | 4 | 4 | 0 | 0 | 0 | 0 | 0 |
| 6 | 500 | 5 | 5 | 5 | 5 | 5 | 5 | 5 | 2 | 2 | 0 | 0 | 1 |
|  | 250 | 4-5 | 4 | 4 | 4 | 5 | 4 | 5 | 0 | 0 | 0 | 0 | 0 |
|  | 125 | 4 | 4 | 4 | 3 | 4 | 3 | 4 | 0 | 0 | 0 | 0 | 0 |
| 7 | 500 | 5 | 5 | 5 | 5 | 5 | 5 | 5 | 2 | 2 | 1 | 0 | 1 |
|  | 250 | 5 | 4-5 | 5 | 4 | 5 | 5 | 5 | 0 | 0 | 0 | 0 | 0 |
|  | 125 | 4 | 4 | 4 | 4 | 4-5 | 4 | 4 | 0 | 0 | 0 | 0 | 0 |
| 8 | 500 | 5 | 5 | 5 | 5 | 5 | 5 | 5 | 2 | 2 | 1 | 0 | 1 |
|  | 250 | 5 | 5 | 5 | 5 | 5 | 5 | 5 | 0 | 0 | 0 | 0 | 0 |
|  | 125 | 5 | 5 | 5 | 4 | 5 | 4 | 4 | 0 | 0 | 0 | 0 | 0 |
| 9 | 500 | 5 | 5 | 5 | 5 | 5 | 5 | 5 | 1 | 1 | 0 | 0 | 0 |
|  | 250 | 4 | 4 | 4 | 4 | 4 | 4 | 4 | 0 | 0 | 0 | 0 | 0 |
|  | 125 | 3 | 3 | 3 | 3 | 3 | 2 | 3 | 0 | 0 | 0 | 0 | 0 |
| 10 | 500 | 5 | 5 | 5 | 5 | 5 | 5 | 5 | 2 | 2 | 0 | 0 | 0 |
|  | 250 | 5 | 4 | 4 | 4 | 5 | 5 | 5 | 0 | 0 | 0 | 0 | 0 |
|  | 125 | 4 | 4 | 4 | 3 | 5 | 4 | 4 | 0 | 0 | 0 | 0 | 0 |
| X (comparison) | 500 | 4 | 4 | 3 | 2 | 4 | 3 | 2 | 1 | 1 | 0 | 0 | 1 |
|  | 250 | 2 | 1 | 0 | 0 | 3 | 2 | 0 | 0 | 0 | 0 | 0 | 0 |
|  | 125 | 0 | 0 | 0 | 0 | 0 | 0 | 0 | 0 | 0 | 0 | 0 | 0 |
| XI (comparison) | 1000 | 5 | 5 | 5 | 4 | 5 | 5 | 5 | 3 | 4 | 3 | 3 | 2 |
|  | 500 | 3 | 3 | 3 | 2 | 0 | 2 | 2 | 0 | 0 | 0 | 0 | 0 |
|  | 250 | 0 | 0 | 0 | 0 | 0 | 0 | 0 | 0 | 0 | 0 | 0 | 0 |
| XII (comparison) | 500 | 5 | 5 | 5 | 5 | 5 | 5 | 5 | 5 | 5 | 5 | 5 | 5 |
|  | 250 | 5 | 5 | 5 | 5 | 5 | 5 | 5 | 2 | 0 | 3 | 0 | 2 |
|  | 125 | 3 | 3 | 4 | 2 | 2 | 2 | 4 | 0 | 0 | 0 | 0 | 0 |
| XIII (comparison) | 150 | 5 | 5 | 5 | 5 | 5 | 5 | 5 | 4 | 5 | 3 | 2 | 4 |
|  | 100 | 3 | 4 | 5 | 4 | 4 | 5 | 5 | 2 | 3 | 2 | 0 | 2 |
|  | 50 | 2 | 2 | 4 | 4 | 4 | 4 | 4 | 1 | 2 | 1 | 0 | 1 |

Note:
(i) Comparison XIII: 2-chloro-4,6-bis(ethylamino)-S-triazine (commercially available product)
(ii) The other comparison compounds are as identified in the footnotes to Table A.

It will be understood that the specification and examples are illustrative but not limitative of the present invention and that other embodiments within the spirit and scope of the invention will suggest themselves to those skilled in the art.

What is claimed is:

1. Herbicidal composition comprising a herbicidally acceptable inert carrier and, in effective amounts, an amidothionophosphonic acid ester compound of the formula

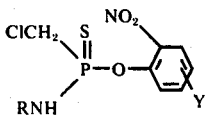

(I)

in which
R is alkyl of from 1 to 6 carbon atoms or lower cycloalkyl of from 5 to 6 carbon atoms; and
Y is halogen or alkyl or alkoxy of from 1 to 6 carbon atoms.

2. Method of combating undesired vegetation, which method comprises applying to said vegetation a herbicidally effective amount of an amidothionophosphonic acid ester compound of the formula

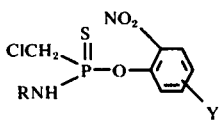

(I)

in which
R is alkyl of from 1 to 6 carbon atoms or lower cycloalkyl; and
Y is halogen or alkyl or alkoxy of from 1 to 6 carbon atoms.

3. Method as claimed in claim 2 wherein R is alkyl of from 1 to 4 carbon atoms, cyclopentyl or cyclohexyl and Y is halogen, alkyl or alkoxy of from 1 to 4 carbon atoms.

4. Method as claimed in claim 2 wherein said compound is selected from the group consisting of:
0-(2-nitro-4-methylphenyl)-N-isopropyl chloromethane thionophosphonamide ester;
0-(2-nitro-4-methylphenyl)-N-cyclohexyl chloromethane thionophosphonamide ester;
0-(2-nitro-4-methylphenyl)-N-n-propyl chloromethane thionophosphonamide ester;
0-(2-nitro-4-methoxyphenyl)-N-isopropyl chloromethane thionophosphonamide ester.

5. Method as claimed in claim 2 wherein said compound is applied to a crop field infested with weeds in an amount that damages the weeds without substantial injury to the crops.

6. Method as claimed in claim 2 wherein, in the formula, R is alkyl of from 1 to 6 carbon atoms.

7. Method as claimed in claim 2 wherein, in the formula, R is lower cycloalkyl of from 5 to 6 carbon atoms.

8. Method as claimed in claim 2 wherein, in the formula, Y is halogen.

9. Method as claimed in claim 2 wherein, in the formula, Y is alkyl of from 1 to 4 carbon atoms.

10. Method as claimed in claim 2 wherein, in the formula, Y is alkoxy of from 1 to 4 carbon atoms.

11. Method as claimed in claim 2 wherein, in the formula, Y is in the 3-position.

12. Method as claimed in claim 2 wherein, in the formula, Y is in the 4-position.

13. Method as claimed in claim 2 wherein, in the formula, Y is in the 5-position.

14. Method as claimed in claim 2 wherein, in the formula, Y is in the 6-position.

15. Method as claimed in claim 2 wherein said compound is 0-(2-nitro-4-methylphenyl)-N-isopropyl chloromethane thionophosphonamide ester.

16. Method as claimed in claim 2 wherein said compound is 0-(2-nitro-4-methylphenyl)-N-cyclohexyl chloromethane thionophosphonamide ester.

17. Method as claimed in claim 2 wherein said compound is 0-(2-nitro-4-methylphenyl)-N-n-propyl chloromethane thionophosphonamide ester.

18. Method as claimed in claim 2 wherein said compound is 0-(2-nitro-4-methoxyphenyl)-N-isopropyl chloromethane thionophosphonamide ester.

* * * * *